United States Patent [19]
Bovet

[11] Patent Number: 4,881,806
[45] Date of Patent: Nov. 21, 1989

[54] AUTOMATIC INTERPUPILLARY DISTANCE MEASURING DEVICE

[75] Inventor: Christian Bovet, Paris, France

[73] Assignee: Essilor International Cie Generale d'Optique, Creteil Cedex, France

[21] Appl. No.: 224,145

[22] Filed: Jul. 26, 1988

[30] Foreign Application Priority Data

Jul. 30, 1987 [FR] France ............................ 87 10804

[51] Int. Cl.[4] .............................................. A61B 3/10
[52] U.S. Cl. ...................................... 351/204; 351/210
[58] Field of Search ............... 351/204, 205, 221, 210, 351/246

[56] References Cited

U.S. PATENT DOCUMENTS 4,591,246  5/1986  Cousyn et al. ........................ 351/204

FOREIGN PATENT DOCUMENTS 0115723  8/1984  European Pat. Off. .
1506352  12/1967  France .

Primary Examiner—P. M. Dzierzynski
Attorney, Agent, or Firm—Charles E. Brown; Charles A. Brown

[57] ABSTRACT

To measure automatically a distance related to the interpupillary distance of a person, a light source generates a corneal reflection on at least one eye of the person. By means of a scanning system such as a rotating mirror, a sensor receiver is scanned transversely to the general direction of observation of the person to direct light rays from the corneal reflection or reflections onto the sensor receiver in which is a measurement reference mark relative to which the corneal reflection or reflections is or are located.

26 Claims, 2 Drawing Sheets

AUTOMATIC INTERPUPILLARY DISTANCE MEASURING DEVICE

BACKGROUND OF THE INVENTION

1. Field of the Invention

The present invention is generally concerned with measuring a distance related to the interpupillary distance of a person, either the interpupillary distance directly, or half the corresponding interpupillary distance.

2. Description of the Prior Art

At present this measurement is performed manually, using an interpupillary distance measuring device.

An interpupillary distance measuring device of this kind is described in French patent No. 1 506 352, for example.

It comprises a light source adapted to produce a corneal reflection on at least one of the two eyes of the person concerned, in practice on each of the latter, and a measurement reference mark relative to which the corneal reflection can be located.

In practice two movable markers are provided for this purpose, which are made to coincide with the respective corneal reflections and the distance between which is then measured with the aid of the associated measurement reference mark.

Although this arrangement, somewhat rudimentary and therefore inexpensive, has given and can give further satisfaction, it has the particular disadvantage of requiring reticules to be moved, so that it is a relatively slow process, and the results are conditioned by the skill of the operator.

A general object of the present invention is to provide an arrangement whereby a distance related to the interpupillary distance of a person can be measured in a simple, automatic and therefore rapid way.

SUMMARY OF THE INVENTION

In one aspect, the invention consists in a method for measuring automatically a distance related to the interpupillary distance of a person in which a light source produces a reflection on the cornea of at least one eye of the person, a sensor receiver is scanned across the corneal reflection or reflections in a direction transverse to the general direction of observation of the person, and the corneal reflection or reflections is or are located relative to a measurement reference mark in the sensor receiver.

This scanning makes it possible to register automatically and in a very simple way the presence of the corneal reflection or reflections to be sensed, and it therefore provides the required interpupillary distance information to full scale, irrespective of the distance that the person is located at, within predefined limits, relative to a median plane which is the theoretical plane of the eyes.

The measurement reference mark is preferably formed by a set of reference light sources regularly spaced in a linear array and in practice, the reference light sources being disposed transversely to the general direction of observation, the measurement reference mark is formed by the image of the reference light sources in the receiver, the light rays from the reference light sources being constrained over at least part of their optical path to follow the same trajectory as those from the corneal reflection or reflections.

In an advantageously reliable and economical way, this systematically eliminates the effect on the results obtained of inevitable variations in the scanning characteristics and/or the eyepiece that is used to form the required images, without this scanning and/or this eyepiece needing to be implemented in an accurate and therefore expensive way.

In outline, the arrangement in accordance with the invention combines with quick and easy implementation the advantage of inexpensive construction.

In another aspect, the invention consists in an interpupillary distance measuring device comprising a light source adapted to produce a reflection on the cornea of at least one eye of a person, a sensor receiver, a scanning device for scanning the sensor receiver transversely to a general direction of observation of the person so as to direct onto the receiver the light rays corresponding to the corneal reflection or reflections, and means for producing in the sensor receiver a measurement reference mark relative to which the position of the corneal reflection or reflections can be determined.

This interpupillary distance measuring device is advantageously compact and also offers high performance in terms of light energy with very economical use since it employs only point light sources each of which is turned on only briefly, although providing very strong illumination.

The characteristics and advantages of the invention will emerge from the following description given by way of example only with reference to the appended schematic drawings.

DESCRIPTION OF THE PREFERRED EMBODIMENT

Figure 1:
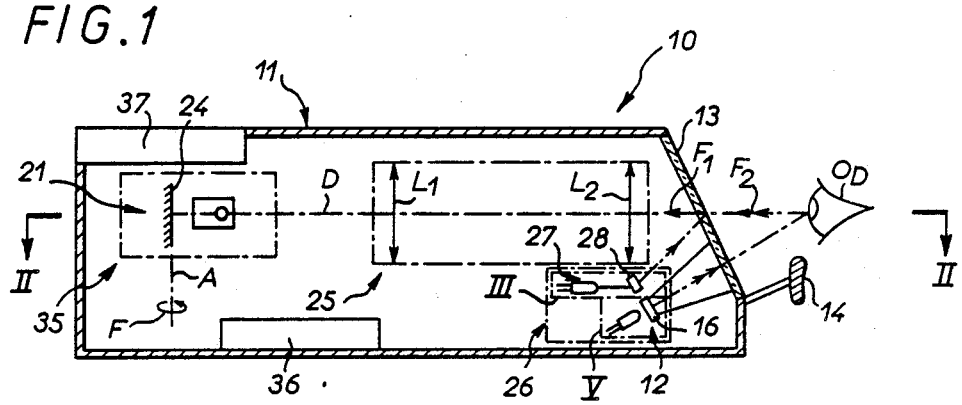
FIG. 1 is an elevation view of an interpupillary distance measuring device in accordance with the invention in cross-section on the line I—I in FIG. 2.
Figure 2:
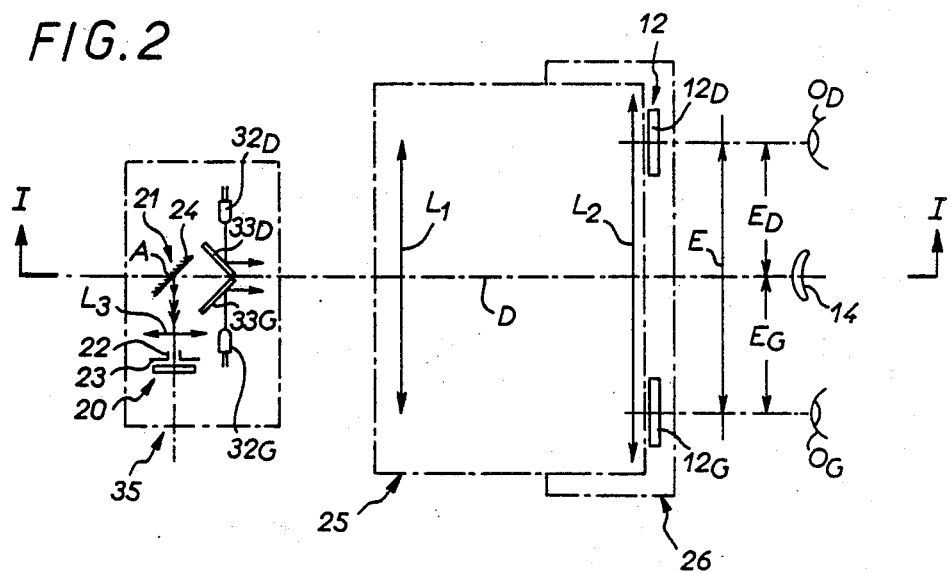
FIG. 2 is a plan view of it on the line II—II in FIG. 1.

In the figures the eyes of the person whose overall interpupillary distance E or interpupillary half-distances ED and EG are to be measured are schematically represented at OD, OG, these distances being measured relative to the person's nasal axis considered here to define the person's general direction of observation D.

The interpupillary distance measuring device 10 used in accordance with the invention to make the corresponding measurement comprises, in a way that is known in itself, in a generally parallelepiped-shape box frame 11 a corneal reflection generator 12, that is to say a light source adapted to generate a corneal reflection on at least one of the eyes OD, OG of the person concerned.

The corneal reflection generator 12 is operative through a simple window 13 common to both eyes OD and OG, closing off the front of the interpupillary distance measuring device 10 and slightly inclined to the general direction of observation D of the person.

This general direction of observation D is coincident with the optical axis of the device.

The frame 11 is fitted with a support against which the person must rest for improved location.

The support shown here is a nose support 14, but a forehead support would be equally suitable.

The corneal reflection generator 12 is offset from the general direction of observation D of the person, being below the general direction of observation D, in the lower part of the frame 11, in the vicinity of the window 13.

It comprises two light sources 12D, 12G each adapted to generate a corneal reflection, one for each eye, the light source 12D for the right eye OD and the light source 12G for the left eye OG.

Each of these light sources 12D, 12G in fact comprises a plurality of elementary light sources 16, of which there are four as shown here, regularly spaced in an array transverse to the general direction of observation D of the person concerned.

The elementary light sources 16 are formed by rectangular openings of specific width formed in the front wall of a respective box 17D, 17G containing the same number of light-emitting diodes 18 spaced by the same distance.

In a way that is known in itself and as will be described in more detail later, the interpupillary distance measuring device 10 in accordance with the invention further comprises a measurement reference mark, which is not visible as such in the figures, relative to which the corneal reflections formed on the right eye OD and on the left eye OG of the person concerned can be located.

The interpupillary distance measuring device 10 comprises a sensor receiver 20 in which the measurement reference mark is operative and a scanning device 21 which is adapted to sweep transversely to the general direction of observation D of the individual, so as to direct onto the sensor receiver 20 the light rays corresponding to the corneal reflections to be sensed.

The sensor receiver 20 is disposed laterally relative to the general direction of observation D of the person. In front of it is a mask 23 comprising a slit 22 controlling access to it. The scanning device 21 comprises a rotatable mirror 24 on said general direction of observation D opposite said sensor receiver 20. As schematically represented by an arrow F in FIG. 1, it is mounted to rotate about an axis A perpendicular to the plane defined by the general direction of observation D and the sensor receiver 20.

An eyepiece 25 comprising two lenses L1, L2 is disposed on the general direction of observation D of the person. The rotatable mirror 24 is placed at the object focus of the eyepiece 25, at least when the measurement to be performed corresponds to distant vision of the person. The theoretical plane of the eyes OD, OG of the person is situated at its image focus, because of the nose support 14.

A lens L3 disposed between the mask 23 and the rotatable mirror 24 forms an image of the slit 22 in the mask 23 situated at infinity.

By virtue of these arrangements, the eyepiece 25 forms an image of the slit 22 in the theoretical plane of the eyes of the person concerned and rotation of the rotatable mirror 24 sweeps the image of the slit 22 transversely to the general direction of observation D of the person.

The corneal reflection generator 12 is part of an emitter 26 further comprising, to form the measurement reference mark, at least one set 27 of reference light sources 28 regularly spaced in a linear array transverse to the general direction of observation D of the person and, like the corneal reflections to be sensed, operated on by the scanning device 21.

Figure 4:
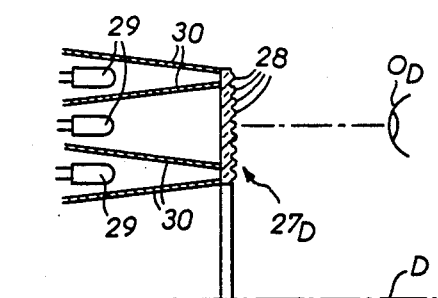
FIG. 4 is a view of the measurement reference mark generator part of which is shown in FIG. 3, to a larger scale and in cross-section on the line IV—IV in FIG. 3.
Figure 4:
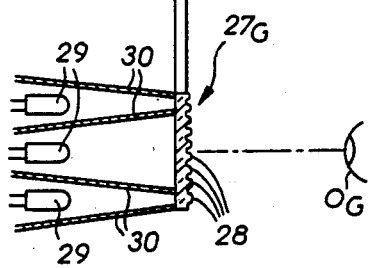
Figure 6:
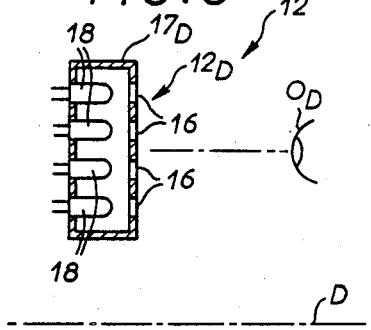
FIG. 6 is a view of the corneal reflection generator part of which is shown in FIG. 5, to the same scale as FIG. 4 and in longitudinal cross-section on the line VI—VI in FIG. 5.
Figure 6:
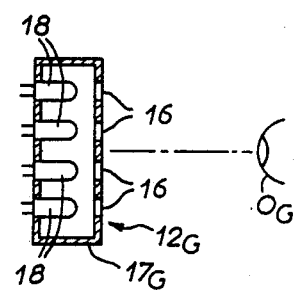

Below the general direction of observation D of the person, and one to each side thereof, are two sets 27D, 27G of reference light sources 28, one for each eye: the set 27D for the right eye OD and the set 27G for the left eye OG (see FIG. 4). There are therefore two elementary measurement reference marks, one for each eye, and a single sensor receiver 20.

Each set 27D, 27G of reference light sources 28 comprises an array of parallel cylindrical microlenses.

These are parallel ribs of semicircular transverse contour projecting from the front surface of a transparent plate, with one rib per reference light source 28. The transparent plate may be shared by both sets 27D, 27G concerned, and may be molded from any synthetic material, for example.

Behind the resulting parallel cylindrical microlenses is at least one light source proper, in the form of a light-emitting diode.

In this instance there are three light-emitting diodes 29 for each set 27D, 27G of reference light sources 28, namely a light-emitting diode 29 for each of the reference light sources 28 disposed at the ends of a set and a light-emitting diode 29 for all the other reference light sources 28 of the latter, with screens 30 extending as far as the corresponding array of microlenses between the light-emitting diodes 29 used in this way.

Over at least part of their optical path the light rays corresponding to the reference light sources 28, schematically represented by a single-headed arrow F1 in FIG. 1, follow the same trajectory as the light rays corresponding to the corneal reflections to be sensed, schematically represented by a double-headed arrow F2.

This applies along all of the general direction of observation D of the person from the window 13 as far as the sensor receiver 20.

Forming part of the emitter 26, like the corneal reflection generator 12, the reference light sources 28 are near the window 13, above said corneal reflection generator 12. The window 13 serves as a reflector for them, to be more precise for the light rays emitted by them.

Like the light rays corresponding to the corneal reflections to be sensed, the light rays corresponding to the reference light sources 28 travel along the general direction of observation D of the person through the eyepiece 25 and are then reflected towards the sensor receiver 20 by the rotating mirror 24 of the scanning device 21.

To fix the gaze of the person the interpupillary distance measuring device 10 in accordance with the invention further comprises at least one supplementary light source and the person is presented with an image of this apparently at infinity when the measurement to be performed is to correspond to distant vision.

Two such supplementary light sources 32D, 32G are in fact provided, one for each eye, the supplementary light source 32D for the right eye OD and the supplementary light source 32G for the left eye OG. Their respective images are visible only to the corresponding eye.

To this end the supplementary light sources 32D, 32G are placed on respective sides of the general direction of observation D of the person, facing each other, between the eyepiece 25 and the rotating mirror 24 of the scanning device 21. Each is operative through the intermediary of a respective thin clear plate 33D, 33G which provides an image of it situated at the object focus of the eyepiece 25 when the measurement to be performed is to correspond to distant vision.

As previously, the supplementary light sources 32D, 32G may each comprise a light-emitting diode, a green diode, for example.

The sensor receiver 20 is a photosensor, in other words a photodiode.

Together with the scanning device 21, the sensor receiver 20 forms part of a subsystem 35 which is movable along the general direction of observation D of the person to allow for near vision measurements as well as distant vision measurements.

Taken overall, the imaging of the slit 22 in the mask 23 is not affected by movement of the subsystem 35.

As a corollary to this, the eyepiece 25 may be fixed, which is advantageous. The supplementary light sources 32D, 32G used to fix the gaze of the person preferably also form part of the mobile subsystem 35, together with the thin clear plates 33D, 33G associated with them, as shown here.

In ways that will be evident to those skilled in the art and which do not of themselves form any part of the present invention and will not therefore be described in detail here, the interpupillary distance measuring device 10 in accordance with the invention further comprises power supply means adapted to energize the various diodes used and the motor which rotates the rotating mirror 24 of the scanning device 21, an electronic control unit 36 for controlling the device as a whole (see FIG. 1) and display means 37 for showing the results obtained.

Figure 7:
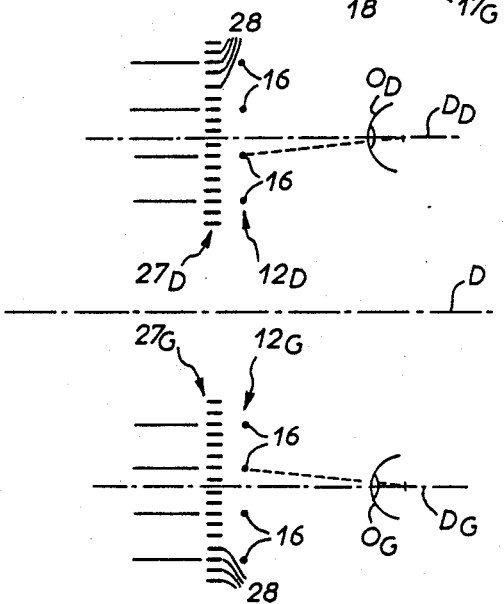
FIG. 7 is a diagram illustrating the use of the interpupillary distance measuring device in accordance with the invention.

As schematically represented by the dashes in FIG. 7, each of the cylindrical microlenses constituting the reference light sources 28 produces an image of the light-emitting diode 29 assigned to it in the form of a luminous straight line segment.

In other words, the reference light sources 28 are in the form of parallel luminous straight line segments.

Each of the elementary light sources 16 constituting the corneal reflection generator 12 is in the form of a light spot, imaging the aperture which formed it.

Each of the elementary light sources 16 creates a corneal reflection in turn.

By virtue of the scanning device 21, or to be more precise by virtue of synchronization between the sweep it performs and the energization of the elementary light sources 16, the corneal reflection processed by the sensor receiver 20 is that created by the elementary light source 16 nearest the particular direction of observation DD, DG of the corresponding eye OD, OG (FIG. 7).

To measure the interpupillary half-distances ED, EG relative to the general direction of observation D of the person, with reference to a conversion table, it suffices to locate the corneal reflections formed in this way relative to the reference light sources 28 and in the corresponding particular observation directions DD, DG, which are parallel to the general direction of observation D.

The interpupillary distance E is the sum of these interpupillary half-distances ED, EG.

The corresponding measurement is performed in the sensor receiver 20, by means of the eyepiece 25 and the scanning device 21.

This is why the measurement reference mark consists of the image of the reference light sources 28 in the sensor receiver 20.

Figure 8A:
FIGS. 8A and 8B are diagrams showing the general nature of the signals delivered by the sensor receiver incorporated in this interpupillary distance measuring device.
Figure 8B:
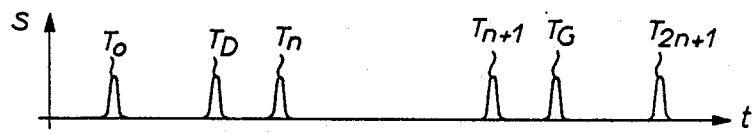
Figure 3:
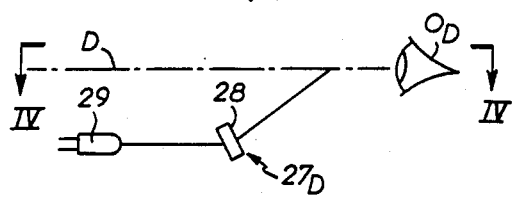
FIG. 3 shows to a larger scale the detail of FIG. 1 marked III on FIG. 1.
Figure 5:
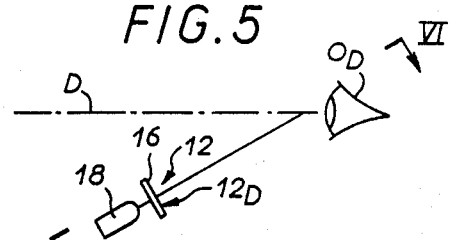
FIG. 5 shows to the same scale as FIG. 3 the detail from FIG. 1 marked V on FIG. 1.

The measurement is performed in two stages, as shown in FIGS. 8A and 8B, in which the amplitude of the signal S delivered by the sensor receiver 20 is plotted on the vertical axis as a function of time t plotted on the horizontal axis.

In a first stage (FIG. 8A) only the measurement reference mark is directed into the sensor receiver 20.

In other words, during this first stage, only the reference light sources 28 are active, with only the light-emitting diodes 29 from which they are derived being energized.

Because of the scanning effect of the rotating mirror 24, the signal delivered by the sensor receiver 20 comprises a succession of peaks T, one for each reference light source 28.

The peaks $T_0$ through $T_n$ correspond to the set 27D of reference light sources 28, and therefore to the right eye OD of the person, and the peaks $T_{n+1}$ through $T_{2n+1}$ correspond to the set 27G of reference light sources 28, and therefore to the left eye OG of the person.

The values corresponding to these peaks $T_0$ through $T_{2n+1}$ are memorized.

This first stage therefore serves to register, so to speak, the geometry of the measurement reference mark used and the measurement reference mark formed and registered in this way is memorized between the first and second stages.

In the second stage, and still due to the scanning effect of the rotating mirror 24, a fraction of the measurement reference mark and the corneal reflections to be sensed are superimposed in the sensor receiver 20.

In this second phase, in which the measurement proper is performed, only the ends of the measurement reference mark are used.

In other words, at this time only the reference light sources 28 at the ends of the sets 27D, 27G are operative, only the corresponding light-emitting diodes 29 being energized.

The signal delivered by the sensor receiver 20 therefore comprises, for the measurement reference mark, only the peaks $T_0$ and $T_n$, on the one hand and $T_{n+1}$ and $T_{2n+1}$, on the other hand, corresponding to the end reference light sources 28.

However, as the corneal reflection generator 12 is active, there appear, between these peaks, peaks TD, TG respectively corresponding to the corneal reflection on the right eye OD and that on the left eye OG of the person.

A rule of three calculation serves to determine the position of these peaks TD, TG relative to the previously memorised peaks $T_0$ through $T_{2n+1}$.

As will be readily understood, any irregularity in the geometry of the measurement reference mark, due for example to cyclic fluctuation in the rotation speed of the motor driving the rotating mirror 24, can therefore have no effect on the accuracy of the measurement performed.

The rotating mirror 24 preferably rotates always in the same direction.

As an alternative to this, however, it can rotate one way for the first stage, that serving to register the geometry of the measurement reference mark, and in the opposite direction for the second stage, that during which the corneal reflections to be sensed are located relative to the measurement reference mark.

The fact that only the end reference light sources are used during the second stage prevents the corneal reflections being masked by any of the intermediary reference light sources.

The various light sources employed must obviously for preference be energized in synchronism with the sweeping performed by the scanning system.

It is therefore desirable for any variations in the average rotation speed of the rotating mirror 24 between the two stages to be low.

The accuracy of the interpupillary distance measuring device 10 in accordance with the invention depends in particular on the geometry of the cylindrical microlenses used to form the measurement reference mark.

In practice, an accuracy of ±0.25 minutes of angle is sufficient for correct mounting of lenses on an eyeglass frame.

The effect of the geometry of these cylindrical microlenses on the accuracy of the interpupillary distance measuring device 10 in accordance with the invention is therefore not decisive.

As for its sensitivity, this depends in particular on the width of the slit 22 providing access to the sensor receiver 20.

This is not critical either, however.

The present invention is not limited to the embodiment described and shown, but encompasses any variant execution thereof.

Also, rather than measuring the interpupillary distance of the person concerned directly, any distance related in a known way to this interpupillary distance may be measured instead.

I claim:

1. Automatic interpupillary distance measuring device, comprising a light source adapted to produce a reflection or reflections on the cornea of at least one eye of a person, a sensor receiver, a scanning device for scanning said sensor receiver transversely to a general direction of observation of the person so as to direct onto said receiver the light rays corresponding to said corneal reflection or reflections, a slit disposed optically between the scanning device and the sensor receiver and providing access to the sensor receiver, and means for producing in said sensor receiver a measurement reference mark relative to which the position of the corneal relection or reflections can be determined.

2. Device according to claim 1, wherein said receiver is disposed laterally relative to said general direction of observation and said scanning device comprises a mirror on said general direction of observation opposite said receiver rotatable about an axis perpendicular to the plane defined by said general direction of observation and receiver.

3. Device according to claim 2, comprising an eyepiece on said general direction of observation and wherein said mirror is located at the object focus of said eyepiece when the measurement to be performed corresponds to distant vision.

4. Device according to claim 3, wherein said eyepiece is fixed.

5. Device according to claim 1, wherein said receiver and said scanning device are parts of a subsystem movable along said general direction of observation.

6. Device according to claim 5, comprising at least one further light source adapted to form an image at infinity to be viewed by said person so as to fix his or her gaze, said at least one supplementary light source comprising part of said movable subsystem.

7. Device according to claim 1 comprising at least one supplementary light source adapted to form an image at infinity to be viewed by said person so as to fix his or her gaze.

8. Device according to claim 7, comprising two supplementary light sources, each adapted to form an image at infinity to be viewed by only one eye of said person.

9. Device according to claim 1, wherein said light source forms said corneal reflection or reflections directly or via a window.

10. Device according to claim 1, wherein said light source comprises a plurality of elementary light sources in a linear array transverse to said general direction of observation.

11. Device according to claim 1, comprising two light sources adapted to produce two corneal reflections, one on each eye of said person.

12. Device according to claim 1, wherein said measurement reference mark is formed by a set of reference light sources regularly spaced in a linear array and said scanning device is operative on said measurement reference mark and on said corneal reflection or reflections.

13. Device according to claim 12, wherein the light rays from said reference light sources are constrained over at least part of their optical path to follow the same trajectory as those from said corneal reflection or reflections.

14. Device according to claim 13, comprising a window through which said light source produces said corneal reflection or reflections and which serves as a reflector for light from said reference light sources, which are disposed near said window.

15. Device according to claim 12, wherein said reference light sources are formed by an array of parallel cylindrical microlenses and at least one light source proper behind said microlenses.

16. Device according to claim 12, comprising two sets of reference light sources, one for each eye of said person.

17. Device according to claim 1, wherein said receiver is a photosensor.

18. Method for measuring automatically a distance related to the interpupillary distance of a person, comprising the steps of: directing a light source at at least one of the person's eyes to produce a corneal reflection or reflections; receiving the corneal reflection or reflections at a sensor receiver; providing a measurement reference mark in the sensor receiver for determining the relative position of the corneal reflection or reflections; providing access to the sensor receiver by slit means; and scanning the corneal reflection or reflections by displacing the image of the slit in the direction transverse to the general direction of observation of the person.

19. Method according to claim 18, comprising forming the measurement reference mark by a set of reference light sources regularly spaced in a linear array.

20. Method according to claim 19, wherein the reference light sources are disposed transversely to said general direction of observation of the person and the measurement reference mark is formed by the image of said reference light sources in the receiver, the light rays from said reference light sources being constrained over at least part of their optical path to follow the same trajectory as those from the corneal reflection or reflections.

21. Method according to claim 19, wherein during a first stage, only the measurement reference mark is directed onto said receiver and during a second stage part, only a fraction of the measurement reference mark and the corneal reflection or reflections are superimposed in the receiver.

22. Method according to claim 21, wherein the fraction of the measurement reference mark is limited to both ends thereof.

23. Method according to claim 22, wherein the measurement reference mark is stored between the first and second stages.

24. Method according to claim 18, wherein there is a measurement reference mark for each eye of the person, and a single sensor receiver.

25. Automatic interpupillary distance measuring device, comprising a light source adapted to be directed at at least one of the eyes of a person to produce a corneal reflection or reflections on the cornea of the person's eye or eyes, a sensor receiver arranged to receive the corneal reflection or reflections, the sensor receiver having a measurement reference mark for determining the relative position of the corneal reflection or reflections, a slit provising access to the sensor receiver, means for forming an image of the slit and means fror scanning the corneal reflection or reflections comprising means for displacing the image of the slit transversely to the general viewing direction of the person.

26. Device according to claim 25, wherein said sensor receiver is disposed laterally relative to the general viewing direction and said means for scanning comprises a mirror located along the general viewing direction and facing said sensor reciever, said mirror being pivotable about an axis perpendicular to a plane defined by the general viewing direction and the direction transverse to the general viewing direction.

* * * * *